(12) United States Patent
Richelsoph et al.

(10) Patent No.: US 7,628,799 B2
(45) Date of Patent: Dec. 8, 2009

(54) ROD TO ROD CONNECTOR

(75) Inventors: Marc Richelsoph, Memphis, TN (US); John A. Usher, West Palm Beach, FL (US)

(73) Assignee: Aesculap AG & Co. KG, Tuttlingen (DE)

( * ) Notice: Subject to any disclaimer, the term of this patent is extended or adjusted under 35 U.S.C. 154(b) by 666 days.

(21) Appl. No.: 11/221,512

(22) Filed: Sep. 8, 2005

(65) Prior Publication Data

US 2007/0049932 A1 Mar. 1, 2007

Related U.S. Application Data

(60) Provisional application No. 60/710,389, filed on Aug. 23, 2005.

(51) Int. Cl.
*A61B 17/70* (2006.01)

(52) U.S. Cl. .................................... 606/250

(58) Field of Classification Search ............... 606/250, 606/251, 252, 253
See application file for complete search history.

(56) References Cited

U.S. PATENT DOCUMENTS 3,865,105 A 2/1975 Lode (Continued)

FOREIGN PATENT DOCUMENTS

DE 39 24 050 A1 1/1991

(Continued)

OTHER PUBLICATIONS

U.S. Appl. No. 11/937,915, filed Nov. 9, 2007, Usher.

(Continued)

*Primary Examiner*—Eduardo C Robert
*Assistant Examiner*—Elana B Fisher
(74) *Attorney, Agent, or Firm*—RatnerPrestia

(57) ABSTRACT

The invention is a rod to rod connector that can be used to interconnect two generally parallel spinal rods of a spinal rod and anchor system. The connector comprises a transverse rod and two pairs of clamping bodies, one for each spinal rod. Each pair connects one of the longitudinal spinal rods to the transverse rod in infinitely adjustable angular relationship. One of the two clamping bodies of each pair comprises a C-shaped channel for accepting the spinal rod. The channel is in communication with a slot that defines a hinge. A threaded screw hole passes transversely through the slot and permits a screw to squeeze the hinge, thereby causing the C-shaped channel to close around and clamp the rod. The second clamping body is similar to the first except that there is no slot or hinge and the screw hole preferably is not threaded, but includes a countersink for seating a chamfered screw head. Also, an angular portion of the screw hole intersects the C-shaped channel. The two clamping bodies are aligned with each other so that their screw holes are coaxial so that a single screw can pass through both holes thereby clamping both rods in the C-shaped channels and fixing the angle between the two clamping bodies and, hence, the two rods. The first clamp clamps the spinal rod by squeezing the hinge to cause the C-shaped channel to squeeze around the rod. The second clamp clamps the transverse rod by virtue of the bottom of the screw head bearing down on the transverse rod over the portion of the screw hole that intersects the C-shaped channel.

9 Claims, 7 Drawing Sheets

U.S. PATENT DOCUMENTS

| | | | |
|---|---|---|---|
| 4,349,017 A | 9/1982 | Sayegh | |
| 4,361,144 A | 11/1982 | Slatis | |
| 4,483,334 A | 11/1984 | Murray | |
| 4,648,388 A | 3/1987 | Steffee | |
| 4,719,905 A | 1/1988 | Steffee | |
| 4,747,400 A | 5/1988 | Koeneman | |
| 4,768,524 A | 9/1988 | Hardy | |
| 4,794,918 A | 1/1989 | Wolter | |
| 4,944,743 A | 7/1990 | Gotzen | |
| 5,002,542 A | 3/1991 | Frigg | |
| 5,005,562 A | 4/1991 | Cotrel | |
| 5,030,220 A | 7/1991 | Howland | 606/61 |
| 5,053,034 A | 10/1991 | Olerud | |
| 5,074,864 A | 12/1991 | Cozad | |
| 5,084,048 A | 1/1992 | Jacob | |
| 5,084,049 A | 1/1992 | Asher et al. | |
| 5,098,432 A | 3/1992 | Wagenknecht | |
| 5,102,412 A | 4/1992 | Rogozinski | |
| 5,112,232 A | 5/1992 | Cray et al. | |
| 5,116,334 A | 5/1992 | Cozad | |
| 5,147,359 A | 9/1992 | Cozad | |
| 5,154,718 A | 10/1992 | Cozad | |
| 5,176,678 A | 1/1993 | Tsou | |
| 5,181,917 A | 1/1993 | Rogozinski | |
| 5,196,013 A | 3/1993 | Harms | |
| 5,201,374 A | 4/1993 | Rahm | |
| 5,207,678 A | 5/1993 | Harms | |
| 5,254,118 A | 10/1993 | Mirkovic | |
| 5,257,993 A | 11/1993 | Asher | |
| 5,261,907 A | 11/1993 | Vignaud et al. | |
| 5,261,913 A | 11/1993 | Marnay | |
| 5,275,600 A | 1/1994 | Allard | |
| 5,304,179 A | 4/1994 | Wagner | |
| 5,306,275 A | 4/1994 | Bryan | |
| 5,312,405 A | 5/1994 | Korotko et al. | |
| 5,330,473 A | 7/1994 | Howland | |
| 5,334,203 A | 8/1994 | Wagner | |
| 5,352,224 A | 10/1994 | Westermann | |
| 5,374,267 A | 12/1994 | Siegal | |
| 5,380,325 A | 1/1995 | Lahille | |
| 5,382,248 A | 1/1995 | Jacobson | |
| 5,395,370 A | 3/1995 | Muller | |
| 5,397,363 A | 3/1995 | Gelbard | |
| 5,403,316 A | 4/1995 | Ashman | |
| 5,413,602 A | 5/1995 | Metz-Stavenhagen | |
| 5,437,669 A | 8/1995 | Yuan | |
| 5,468,241 A | 11/1995 | Metz-Stavenhagen | |
| 5,470,333 A | 11/1995 | Ray | |
| 5,474,551 A * | 12/1995 | Finn et al. | 606/264 |
| 5,474,555 A | 12/1995 | Puno | |
| 5,476,464 A | 12/1995 | Metz-Stavenhagen et al. | |
| 5,487,742 A | 1/1996 | Cotrel | |
| 5,498,263 A | 3/1996 | DiNello et al. | |
| 5,507,745 A | 4/1996 | Logroscino | |
| 5,507,746 A | 4/1996 | Lin | |
| 5,514,132 A | 5/1996 | Csernatony | |
| 5,522,816 A | 6/1996 | Dinello et al. | |
| 5,527,314 A | 6/1996 | Brumfield | |
| 5,531,745 A | 7/1996 | Ray | |
| 5,531,747 A | 7/1996 | Ray | |
| 5,534,002 A | 7/1996 | Brumfield | |
| 5,536,268 A | 7/1996 | Griss | |
| 5,545,164 A | 8/1996 | Howland | |
| 5,545,166 A | 8/1996 | Howland | |
| 5,545,167 A | 8/1996 | Lin | |
| 5,549,607 A | 8/1996 | Olson | |
| 5,562,660 A | 10/1996 | Grob | |
| 5,562,662 A | 10/1996 | Brumfield | |
| 5,562,663 A | 10/1996 | Wisnewski | |
| 5,569,246 A | 10/1996 | Ojima | |
| 5,569,247 A | 10/1996 | Morrison | |
| 5,578,034 A * | 11/1996 | Estes | 606/281 |
| 5,601,552 A | 2/1997 | Cotrel | |
| 5,609,594 A | 3/1997 | Errico | |
| 5,609,992 A | 3/1997 | Sorori | |
| 5,611,800 A | 3/1997 | Davis et al. | |
| 5,613,968 A | 3/1997 | Lin | |
| 5,620,444 A | 4/1997 | Assaker | |
| 5,624,442 A | 4/1997 | Mellinger et al. | |
| 5,630,816 A | 5/1997 | Kambin | |
| 5,643,259 A | 7/1997 | Sasso | |
| 5,651,789 A | 7/1997 | Cotrel | |
| 5,653,708 A | 8/1997 | Howland | |
| 5,667,506 A | 9/1997 | Sutterlin | |
| 5,667,507 A | 9/1997 | Corin | |
| 5,669,910 A | 9/1997 | Korhonen et al. | |
| 5,672,176 A | 9/1997 | Biedermann | |
| 5,676,665 A | 10/1997 | Bryan | |
| 5,676,703 A | 10/1997 | Gelbard | |
| 5,683,393 A | 11/1997 | Ralph | |
| 5,688,272 A | 11/1997 | Montague et al. | |
| 5,688,275 A | 11/1997 | Koros | |
| 5,702,393 A * | 12/1997 | Pfaifer | 606/328 |
| 5,702,452 A | 12/1997 | Argenson | |
| 5,707,372 A | 1/1998 | Errico | |
| 5,709,684 A | 1/1998 | Errico | |
| 5,709,685 A | 1/1998 | Dombrowski | |
| 5,716,355 A | 2/1998 | Jackson et al. | |
| 5,716,356 A | 2/1998 | Biedermann | |
| 5,727,899 A | 3/1998 | Dobrovolny | |
| 5,733,285 A | 3/1998 | Errico | |
| 5,733,286 A | 3/1998 | Errico | |
| 5,735,850 A | 4/1998 | Baumgartner | |
| 5,735,851 A | 4/1998 | Errico | |
| 5,735,853 A | 4/1998 | Olerud | |
| 5,741,254 A | 4/1998 | Henry et al. | |
| 5,741,255 A | 4/1998 | Krag | |
| 5,743,911 A | 4/1998 | Cotrel | |
| 5,746,741 A | 5/1998 | Kraus et al. | |
| 5,752,955 A | 5/1998 | Errico | |
| 5,800,548 A | 9/1998 | Martin et al. | |
| 5,810,816 A | 9/1998 | Roussouly | |
| 5,814,046 A | 9/1998 | Hopf | |
| 5,855,284 A | 1/1999 | Dembicks | |
| 5,876,403 A | 3/1999 | Shitoto | |
| 5,899,903 A | 5/1999 | Cotrel | |
| 5,928,231 A | 7/1999 | Klein | |
| 5,938,663 A | 8/1999 | Petreto | |
| 5,947,965 A | 9/1999 | Bryan | |
| 5,947,966 A | 9/1999 | Drewry et al. | |
| 5,947,967 A | 9/1999 | Barker | |
| 5,976,133 A | 11/1999 | Kraus et al. | |
| 5,976,135 A | 11/1999 | Sherman | |
| 5,980,521 A | 11/1999 | Montague | |
| 5,980,523 A | 11/1999 | Jackson | |
| 5,984,922 A | 11/1999 | McKay | |
| 5,984,923 A | 11/1999 | Breard | |
| 5,984,924 A | 11/1999 | Asher | |
| 5,989,251 A | 11/1999 | Nichols | |
| 5,989,350 A | 11/1999 | Fischer et al. | |
| 5,997,539 A | 12/1999 | Errico | |
| 6,027,533 A | 2/2000 | Olerud | |
| 6,030,388 A | 2/2000 | Yoshimi | |
| 6,050,997 A | 4/2000 | Mullane | |
| 6,063,090 A | 5/2000 | Schlapfer | |
| 6,077,262 A | 6/2000 | Schlapfer | |
| 6,080,156 A | 6/2000 | Asher | |
| 6,083,226 A | 7/2000 | Fiz | |
| 6,090,110 A | 7/2000 | Metz-Stavenhagen | |
| 6,096,039 A | 8/2000 | Stoltenberg | |
| 6,110,173 A | 8/2000 | Thomas | |
| 6,113,600 A | 9/2000 | Drummond et al. | |
| 6,113,601 A | 9/2000 | Tatar | |
| 6,132,430 A | 10/2000 | Wagner | |

| | | | | | | |
|---|---|---|---|---|---|---|
| 6,136,003 | A | 10/2000 | Hoeck | 6,740,086 B2 | 5/2004 | Richelsoph |
| 6,139,548 | A | 10/2000 | Errico | 6,749,361 B2 | 6/2004 | Hermann et al. |
| 6,171,311 | B1 | 1/2001 | Richelsoph | 6,749,612 B1 | 6/2004 | Conchy et al. |
| 6,176,861 | B1 | 1/2001 | Bernstein | 6,749,613 B1 | 6/2004 | Conchy et al. |
| 6,179,838 | B1 | 1/2001 | Fiz | 6,758,545 B2 | 7/2004 | Ikeda |
| 6,179,841 | B1 | 1/2001 | Jackson | 6,770,075 B2 | 8/2004 | Howland |
| 6,183,473 | B1 | 2/2001 | Ashman | 6,773,214 B2 | 8/2004 | Jakubowski, Jr. et al. |
| 6,187,005 | B1 | 2/2001 | Brace | 6,783,526 B1 | 8/2004 | Lin et al. |
| 6,210,413 | B1 | 4/2001 | Justis | 6,786,907 B2 | 9/2004 | Lange |
| 6,214,006 | B1 | 4/2001 | Metz Stavenhagen | 6,872,208 B1 | 3/2005 | McBride et al. |
| 6,217,578 | B1 | 4/2001 | Crozet | 6,872,209 B2 | 3/2005 | Morrison |
| 6,231,575 | B1 | 5/2001 | Krag | 6,875,211 B2 | 4/2005 | Nichols et al. |
| 6,234,705 | B1 | 5/2001 | Troxell | 6,887,241 B1 | 5/2005 | McBride et al. |
| 6,238,396 | B1 | 5/2001 | Lombardo | 6,964,665 B2 | 11/2005 | Thomas |
| 6,254,602 | B1 | 7/2001 | Justis | 7,008,423 B2 | 3/2006 | Assaker |
| 6,254,603 | B1 | 7/2001 | Gertzbein | 7,033,358 B2 | 4/2006 | Taylor et al. |
| 6,258,090 | B1 | 7/2001 | Jackson | 7,081,116 B1 | 7/2006 | Carli |
| 6,261,287 | B1 | 7/2001 | Metz Stavenhagen | 7,122,036 B2 | 10/2006 | Vanacker |
| 6,264,658 | B1 | 7/2001 | Lee | 7,128,743 B2 | 10/2006 | Metz-Stavenhagen |
| 6,267,765 | B1 | 7/2001 | Taylor | 7,137,986 B2 | 11/2006 | Troxell et al. |
| 6,273,888 | B1 | 8/2001 | Justis | 7,166,108 B2 | 1/2007 | Mazda et al. |
| 6,280,442 | B1 | 8/2001 | Barker | 7,270,665 B2 | 9/2007 | Morrison |
| 6,280,443 | B1 | 8/2001 | Gu | 7,314,467 B2 | 1/2008 | Howland |
| 6,280,445 | B1 | 8/2001 | Morrison | 7,322,979 B2 | 1/2008 | Crandall |
| 6,283,967 | B1 | 9/2001 | Troxell | 2002/0035366 A1 | 3/2002 | Walder |
| 6,287,308 | B1 | 9/2001 | Betz | 2002/0111625 A1* | 8/2002 | Richelsoph et al. ........... 606/61 |
| 6,287,309 | B1 | 9/2001 | Baccelli | 2002/0143327 A1 | 10/2002 | Shluzas |
| 6,287,311 | B1 | 9/2001 | Sherman | 2003/0004512 A1 | 1/2003 | Farris |
| 6,290,700 | B1 | 9/2001 | Schmotzer | 2003/0060823 A1 | 3/2003 | Bryan |
| 6,290,703 | B1 | 9/2001 | Ganem | 2003/0114853 A1 | 6/2003 | Burgess et al. |
| 6,299,614 | B1 | 10/2001 | Kretschmer | 2004/0044344 A1 | 3/2004 | Winquist |
| 6,302,882 | B1 | 10/2001 | Lin et al. | 2004/0092930 A1 | 5/2004 | Petit et al. |
| 6,302,888 | B1 | 10/2001 | Mellinger | 2004/0116928 A1 | 6/2004 | Young |
| 6,306,137 | B2 | 10/2001 | Troxell | 2004/0133202 A1 | 7/2004 | Suzuki et al. |
| 6,309,135 | B1 | 10/2001 | Thomson et al. | 2004/0133203 A1 | 7/2004 | Young |
| 6,309,390 | B1 | 10/2001 | Le Couedic | 2004/0260285 A1 | 12/2004 | Steib |
| 6,309,391 | B1 | 10/2001 | Crandall | 2005/0080416 A1 | 4/2005 | Ryan et al. |
| 6,326,740 | B1 | 12/2001 | Chang | 2005/0080419 A1 | 4/2005 | Donath |
| 6,328,740 | B1 | 12/2001 | Richelsoph | 2005/0090821 A1 | 4/2005 | Berrevoets et al. |
| 6,328,741 | B1 | 12/2001 | Richelsoph | 2005/0107789 A1 | 5/2005 | Sweeney |
| 6,361,535 | B2 | 3/2002 | Jackson | 2005/0228377 A1 | 10/2005 | Chao et al. |
| 6,368,319 | B1 | 4/2002 | Schaefer | 2006/0058789 A1* | 3/2006 | Kim et al. ..................... 606/61 |
| 6,368,321 | B1 | 4/2002 | Jackson | 2006/0064093 A1 | 3/2006 | Thramann et al. |
| 6,371,957 | B1 | 4/2002 | Amrein | 2006/0084996 A1 | 4/2006 | Metz-Stavenhagen |
| 6,375,657 | B1 | 4/2002 | Doubler | 2006/0206114 A1 | 9/2006 | Ensign et al. |
| 6,379,354 | B1 | 4/2002 | Rogozinski | 2006/0217712 A1 | 9/2006 | Mueller et al. |
| 6,379,357 | B1 | 4/2002 | Bernstein | 2006/0233597 A1 | 10/2006 | Ensign et al. |
| 6,402,751 | B1 | 6/2002 | Hoeck et al. | 2006/0247622 A1 | 11/2006 | Maughan et al. |
| 6,443,953 | B1 | 9/2002 | Perra | 2006/0271051 A1 | 11/2006 | Berrevoets et al. |
| 6,458,132 | B2 | 10/2002 | Choi | 2007/0049932 A1 | 3/2007 | Richelsoph |
| 6,471,705 | B1 | 10/2002 | Biedermann | | | |
| 6,524,310 | B1 | 2/2003 | Lombardo et al. | FOREIGN PATENT DOCUMENTS | | |
| 6,533,789 | B1* | 3/2003 | Hall et al. ................... 606/281 | DE | 2 98 08 593 | 10/1999 |
| 6,537,276 | B2 | 3/2003 | Metz Stavenhagen | DE | 1 99 57 332 | 11/1999 |
| 6,554,832 | B2 | 4/2003 | Shluzas | EP | 0 466 092 | 7/1991 |
| 6,565,568 | B1 | 5/2003 | Rogozinski | EP | 0 536 066 | 9/1992 |
| 6,565,569 | B1* | 5/2003 | Assaker et al. .............. 606/250 | EP | 0 596 788 | 10/1993 |
| 6,569,164 | B1 | 5/2003 | Assaker | EP | 0 734 688 | 2/1996 |
| 6,572,618 | B1 | 6/2003 | Morrison | EP | 0 793 947 A1 | 9/1997 |
| 6,574,789 | B1 | 6/2003 | Yamauchi | EP | 0 836 836 | 4/1998 |
| 6,602,253 | B2 | 8/2003 | Richelsoph et al. | EP | 0 878 170 A2 | 11/1998 |
| 6,610,063 | B2 | 8/2003 | Kumar | EP | 0 956 829 | 11/1999 |
| 6,616,668 | B2 | 9/2003 | Altarac et al. | EP | 1 093 761 | 4/2001 |
| 6,618,960 | B2 | 9/2003 | Brown | EP | 1 103 226 | 5/2001 |
| 6,620,164 | B2 | 9/2003 | Ueyama | EP | 0 746 255 B1 | 9/2002 |
| 6,626,908 | B2 | 9/2003 | Cooper | FR | 2 697 742 | 5/1994 |
| 6,652,535 | B2 | 11/2003 | Kvarnstrom et al. | FR | 2 781 359 A1 | 8/2000 |
| 6,673,073 | B1 | 1/2004 | Schafer | FR | 2 804 314 A1 | 8/2001 |
| 6,685,705 | B1 | 2/2004 | Taylor | WO | 91/01115 | 2/1991 |
| 6,699,248 | B2 | 3/2004 | Jackson | WO | 91/06254 | 5/1991 |
| 6,736,816 | B2 | 5/2004 | Ritland | WO | 93/11715 | 6/1993 |
| 6,736,817 | B2 | 5/2004 | Troxell et al. | WO | 93/21847 | 11/1993 |
| 6,736,820 | B2 | 5/2004 | Biedermann | | | |

| | | | | | | |
|---|---|---|---|---|---|---|
| WO | 94/00062 | 1/1994 | | WO | 00/62691 | 10/2000 |
| WO | 94/00066 | 1/1994 | | WO | 00/62692 | 10/2000 |
| WO | 94/06361 | 3/1994 | | WO | 00/72769 | 12/2000 |
| WO | 94/08530 | 4/1994 | | WO | 00/72770 | 12/2000 |
| WO | 94/14384 | 7/1994 | | WO | 00/76413 | 12/2000 |
| WO | 94/20048 | 9/1994 | | WO | 01/01872 | 1/2001 |
| WO | 95/02372 | 1/1995 | | WO | 01/01873 | 1/2001 |
| WO | 95/08298 | 3/1995 | | WO | 01/06939 | 2/2001 |
| WO | 95/13753 | 5/1995 | | WO | 01/06940 | 2/2001 |
| WO | 95/13754 | 5/1995 | | WO | 01/08574 | 2/2001 |
| WO | 95/13755 | 5/1995 | | WO | 01/10317 | 2/2001 |
| WO | 95/13756 | 5/1995 | | WO | 01/15612 | 3/2001 |
| WO | 95/25473 | 9/1995 | | WO | 01/19266 | 3/2001 |
| WO | 95/26687 | 10/1995 | | WO | 00/54681 | 4/2001 |
| WO | 95/28889 | 11/1995 | | WO | 01/24718 | 4/2001 |
| WO | 95/31147 | 11/1995 | | WO | 01/39677 | 6/2001 |
| WO | 95/35067 | 12/1995 | | WO | 01/52756 | 7/2001 |
| WO | 96/02200 | 2/1996 | | WO | 01/52757 | 7/2001 |
| WO | 96/27334 | 9/1996 | | WO | 01/52758 | 7/2001 |
| WO | 96/28106 | 9/1996 | | WO | 01/54597 | 8/2001 |
| WO | 96/32070 | 10/1996 | | WO | 01/58369 | 8/2001 |
| WO | 96/36291 | 11/1996 | | WO | 01/67972 | 9/2001 |
| WO | 96/39090 | 12/1996 | | WO | 01/67973 | 9/2001 |
| WO | 96/39972 | 12/1996 | | WO | 01/78613 | 10/2001 |
| WO | 96/41582 | 12/1996 | | WO | 01/91656 | 12/2001 |
| WO | 97/06742 | 2/1997 | | WO | 02/00124 | 1/2002 |
| WO | 97/14368 | 4/1997 | | WO | 02/00125 | 1/2002 |
| WO | 97/23170 | 7/1997 | | WO | 02/00126 | 1/2002 |
| WO | 97/31579 | 9/1997 | | WO | 02/02024 | 1/2002 |
| WO | 97/31580 | 9/1997 | | WO | 02/09603 | 2/2002 |
| WO | 97/38640 | 10/1997 | | WO | 02/15766 | 2/2002 |
| WO | 97/43974 | 11/1997 | | WO | 02/30307 | 4/2002 |
| WO | 98/15233 | 4/1998 | | WO | 02/34149 | 5/2002 |
| WO | 98/17188 | 4/1998 | | WO | 02/34151 | 5/2002 |
| WO | 98/37824 | 9/1998 | | WO | 02/38060 | 5/2002 |
| WO | 98/43551 | 10/1998 | | WO | 02/38061 | 5/2002 |
| WO | 98/55038 | 12/1998 | | WO | 02/38063 | 5/2002 |
| WO | 99/00065 | 1/1999 | | WO | 02/41797 | 5/2002 |
| WO | 99/03415 | 1/1999 | | WO | 02/45606 | 6/2002 |
| WO | 99/09901 | 3/1999 | | WO | 02/45607 | 6/2002 |
| WO | 99/15094 | 4/1999 | | WO | 02/078517 | 10/2002 |
| WO | 99/18874 | 4/1999 | | WO | 02/090604 | 11/2002 |
| WO | 99/29248 | 6/1999 | | WO | 02/091931 | 11/2002 |
| WO | 99/49802 | 10/1999 | | WO | 03/037198 | 5/2003 |
| WO | 99/55246 | 11/1999 | | WO | 03/068087 | 8/2003 |
| WO | 99/55247 | 11/1999 | | WO | 03/099148 | 12/2003 |
| WO | 99/56652 | 11/1999 | | WO | 2004/010881 | 2/2004 |
| WO | 00/06038 | 2/2000 | | WO | 2004/021902 | 3/2004 |
| WO | 00/14568 | 3/2000 | | WO | 2004/039268 | 5/2004 |
| WO | 00/15125 | 3/2000 | | WO | 2004/039269 | 5/2004 |
| WO | 00/15126 | 3/2000 | | WO | 2004/096065 | 11/2004 |
| WO | 00/16710 | 3/2000 | | WO | 2004/110289 | 12/2004 |
| WO | 00/21447 | 4/2000 | | WO | 2004/112626 | 12/2004 |
| WO | 00/21477 | 4/2000 | | | | |
| WO | 00/25689 | 5/2000 | | | | |
| WO | 00/42930 | 7/2000 | | | | |
| WO | 00/48523 | 8/2000 | | | | |
| WO | 00/57801 | 10/2000 | | | | |
| WO | 00/59387 A | 10/2000 | | | | |

OTHER PUBLICATIONS

European Search Report, Application No. 06016987.7-1526, dated Feb. 13, 2007.

* cited by examiner

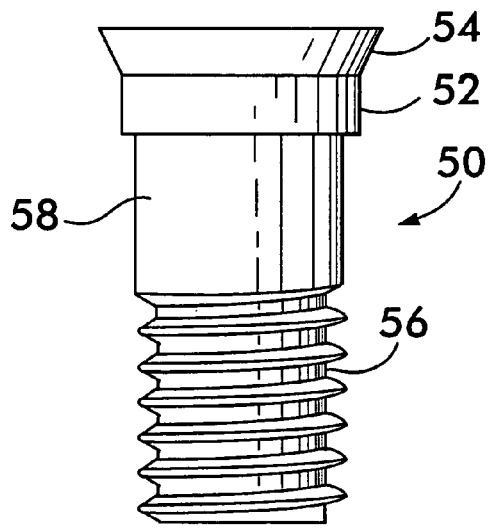
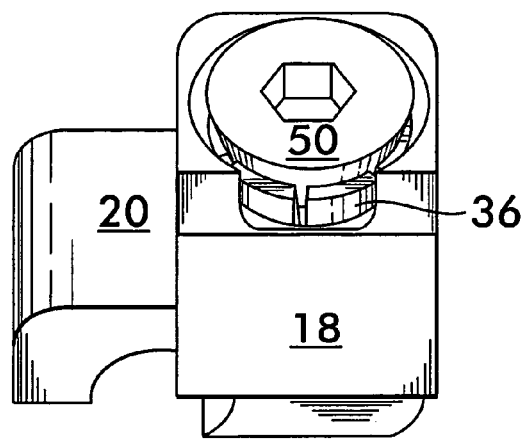
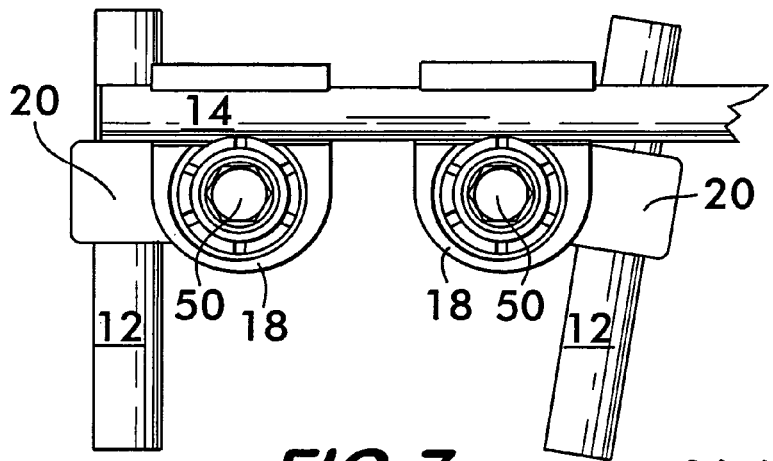
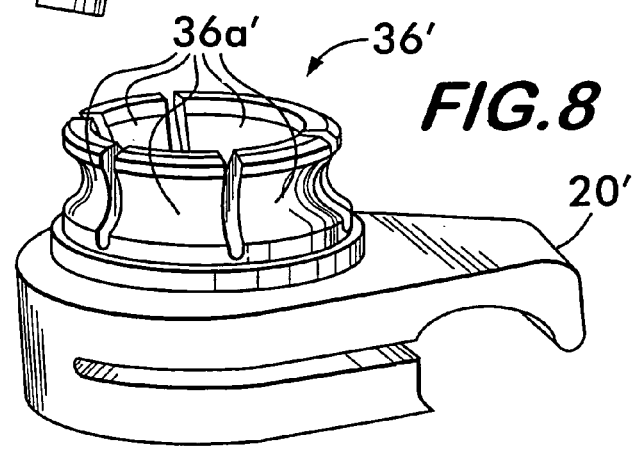

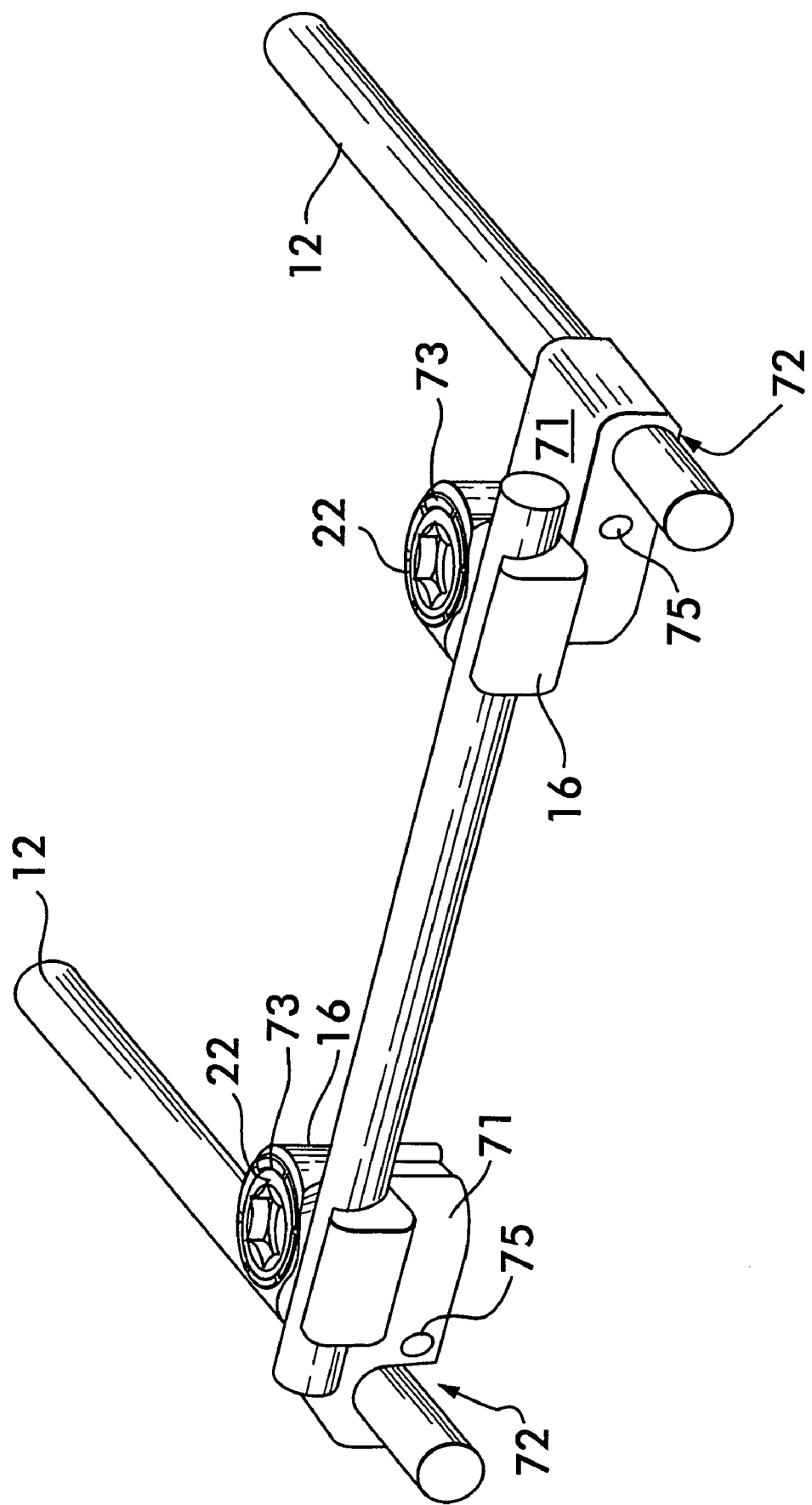

ROD TO ROD CONNECTOR

CROSS REFERENCE TO RELATED APPLICATION

This application claims the priority of U.S. Provisional Application No. 60/710,389, filed Aug. 23, 2005, which is hereby incorporated herein by reference.

BACKGROUND

1. Field of the Invention

The invention generally relates to orthopedic devices. More specifically, the present invention is a surgical tool or medical construct used with spinal rods for the purpose of spinal fixation and correction of spinal curvature.

2. Description of Related Art

Spinal rods are often used for spinal fixation, including for correction of scoliotic curves. Fixation using such rods often involves implantation of rods and attaching them to the spine by anchors in the form of hooks and/or screws. Usually, a pair of rods are placed on opposite sides of the portion of the spine to be fixed.

Various systems have been developed for cross linking spinal rods to prevent rod migration and to increase stiffness of the paired rod assembly.

Many assemblies used for interconnecting spinal rods, commonly referred to as transverse connector assemblies or rod to rod connectors, utilize a plate mechanism having openings therethrough for adjustably retaining hook systems that are bolted in place in the plate. Examples of such systems include U.S. Pat. No. 5,334,203 to Wagner and U.S. Pat. No. 5,522,816 to Dinello et al. U.S. Pat. No. 5,498,263 to Dinello et al., for instance, discloses a transverse connector system utilizing set screws to interconnect vertebrae coupling members while also using plate members as described above for interconnecting the coupling members. A square unit is formed having two sides defined by the plate members and two sides defined by the spaced rods.

U.S. Pat. No. 5,312,405 to Korotko et al. discloses a coupler used for interconnecting spinal rods wherein the coupler itself is a two piece unit. The neck portion of each unit is interconnected by a screw mechanism which clamps a male portion within a female portion of the system. The system also utilizes coupler inserts or yokes which engage a rod and are compressed about the rod when disposed within a seat portion of each coupler and compressed by an instrument which engages the bottom of the rod between the rod and the spine and the top of the coupler.

In further attempts to overcome these problems, various patents have disclosed devices wherein the set screw directly contacts the rod. Examples of such patents include U.S. Pat. No. 6,113,600 to Drummond et al., U.S. Pat. No. 5,624,442 to Mellinger et al., and U.S. Pat. No. 5,601,552 to Cotrel. In these patents, the force required to lock the set screw causes deformation of the rod at the point of contact of the set screw. This is more severe in cases where the set screw tip is conically shaped such as that found in FIG. 6 of the Drummond et al. patent. This causes deeper, more localized deformation and therefore stress inducing indentation that can lower rod fatigue life. Additionally, the depth of the notch, as well as the induced localized stress is subject to random values based on how tight the surgeon tightens the set screw at the time of surgery.

Numerous spinal rod systems have also been developed which provide transverse connectors for linking the adjacent spinal rods across the spinal midline to provide a rigid and stable construct. Most of these systems present one or more difficulties for spinal surgeons. Many of the devices are high profile, which increases soft tissue trauma and surgical complications. Furthermore, in many of these prior art systems, the attachment devices must be preloaded on the spinal rods, which can require significant pre-operative planning and which virtually eliminates the opportunity to add connectors in situ.

One transverse connector system is the TSRH™ CROSSLINK™ of Danek Medical, Inc. The TSRH™ CROSSLINK™ utilizes a three point shear clamp mechanism which restricts motion between the rods in all directions, and particularly resists axial forces between rods and torsional moments about the axis of the rods. A quadrilateral construct is formed by laterally connecting the rods across the sagittal plane with rigid plates. The lateral connection reduces the loss of correction that can occur over time.

Rigid transverse connections between spinal rods are beneficial because they restrict rod migration and increase construct stiffness. In many cases involving multi-level fusion of the spine, these features are highly beneficial while stabilizing the spine construct until fusion in accomplished while solid bone fusion is accomplished. In the post-operative period before fusion occurs, a significant amount of motion can occur between the rods, wires and hooks, which can, for example, allow a scoliotic correlation to decrease or the pelvis to de-rotate toward its previous, deformed position. By providing a rigid transverse connection between two spinal rods, the loss of correction can be reduced and a stiffer construct can be created which may enhance the promotion of a solid fusion. While other devices may provide a good construct, a need has remained for low profile devices where the surface area of contact with the rod is greatly increased and thus minimizes localized stress regardless of how tight the set screw is secured.

It is sometimes the case that the two side by side spinal rods that are to be interconnected by a rod to rod connector are not perfectly parallel to each other. This is a problem for many rod to rod connectors of the prior art which do not permit for any angle between the two spinal rods.

It is an object of the present invention to provide a rod to rod connector that engages a rod by a simple locking mechanism.

It is another object of the present invention to provide a rod to rod connector having few parts and requiring minimal manipulation to assemble and provide the interconnection.

It is a further object of the present invention to provide a rod to rod connector that requires only a simple screw driver or nut driver outside of the assembly for its interconnection between a pair of spinal rods.

It is yet another object of the present invention to develop a rod to rod connector having a surface area of contact with the rod that is greatly increased and thus minimizes localized stress regardless of how tight the set screw is set.

Even further, it is an object of the present invention to provide a rod to rod connector that permits for different angles between two side-by-side spinal rods.

SUMMARY OF THE INVENTION

The invention is a rod to rod connector that, for instance, can be used to interconnect two generally parallel spinal rods of a spinal rod and anchor system. The rod to rod connector comprises a transverse rod and two pairs of clamping bodies, one for each spinal rod. Each pair of clamping bodies connects one of the longitudinal spinal rods to the transverse rod in an infinitely adjustable angular relationship to each other. One of the two clamping bodies of each pair comprises a C-shaped channel for accepting the spinal rod. The channel is in communication with a slot that defines a hinge. A threaded screw hole passes transversely through the slot and permits a screw to squeeze the hinge, thereby narrowing the slot and causing the C-shaped channel to close around and clamp the spinal rod. The second clamping body of each pair is similar to the first except that there is no slot or hinge, and the screw hole preferably is not threaded, but instead includes a countersink for seating a chamfered screw head. Also, an angular portion of the screw hole intersects the C-shaped channel, which accepts the transverse rod.

The two clamping bodies are aligned with each other so that their screw holes are coaxial with each other and a single screw clamps both rods in the C-shaped channels and fixes the angular relationship between the two clamping bodies. The first clamp clamps the spinal rod by squeezing the hinge and slot so as to cause the C-shaped spinal rod channel to squeeze around the rod. The second clamp clamps the transverse rod by virtue of the bottom surface of the screw head bearing down on the rod over the portion of the screw hole that intersects the C-shaped transverse rod channel.

In a preferred embodiment, the first clamp of each pair further comprises a plurality of flanges defining a collar that extends coaxially from the screw hole, which flanges fit within the screw hole of the second clamping body when the two clamping bodies are aligned and joined. The flanges spread outwardly when forced downwardly by a screw head having a chamfered bottom causing the flanges to dig into the interior surface of the screw hole of the other clamping body. This feature provides extra gripping between the two clamping bodies thus providing even greater resistance to any unintentional change in the angle between the spinal rod and the transverse rod once the screw is tightened.

BRIEF DESCRIPTION OF THE DRAWINGS

FIG. 5 is a plan view of a screw for use in connection with the clamping body pair in accordance with the present invention.

FIG. 6 is a perspective view of a clamping body pair in accordance with the present invention joined together by the screw.

FIG. 7 is a plan view of a rod to rod connector in accordance with the present invention being used to interconnect two spinal rods that are not parallel to each other.

FIG. 8 is a perspective view of a lower clamping member in accordance with an alternative embodiment of the present invention.

FIG. 12B is another perspective view of the rod to rod connector of FIG. 12A.

DETAILED DESCRIPTION OF THE INVENTION

Figure 1:
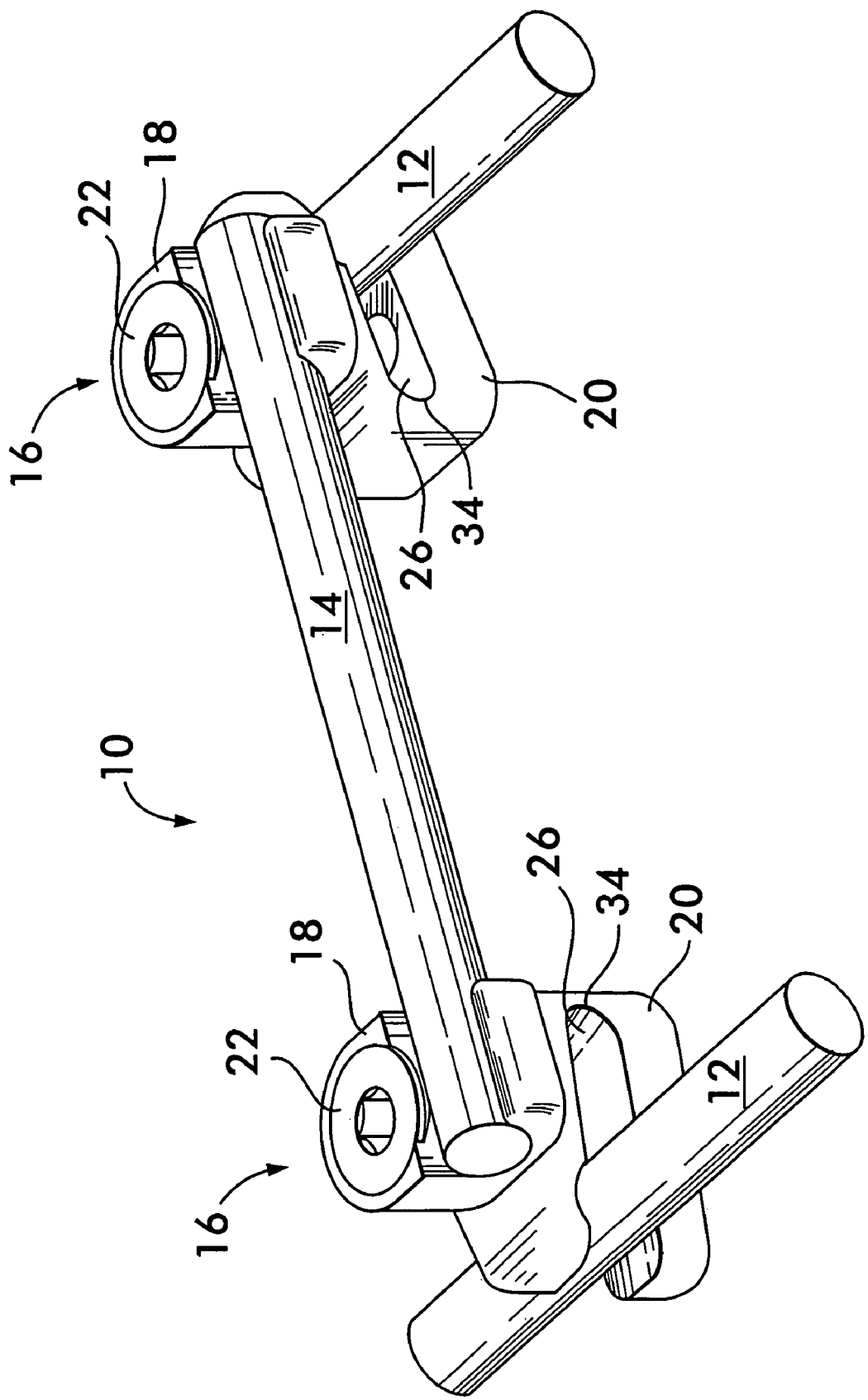
FIG. 1 is a perspective view of a rod to rod connector in accordance with the present invention.

FIG. 1 is a perspective view of a rod to rod connector 10 in accordance with the present invention interconnecting two generally parallel spinal rods 12. The connector 10 comprises a transverse rod 14 and a pair of clamping assemblies 16. Each clamping assembly 16 comprises an upper clamping member 18 and a lower clamping member 20. Preferably, to two upper clamping members 18 are identical to each other and the two lower clamping members 20 are identical to each other. Each clamping assembly 16 further comprises a screw 22. The clamping members 18 and 20 preferably are made of a biocompatible, resilient material such as titanium, stainless steel, or any number of biocompatible polymers.

Figure 2A:
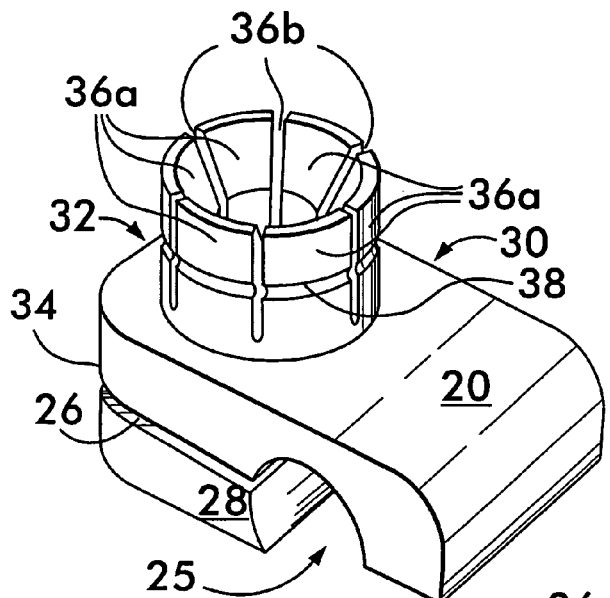
FIGS. 2A and 2B are perspective views from two different perspectives of the lower clamping body of a clamping body pair of FIG. 1.
Figure 2B:
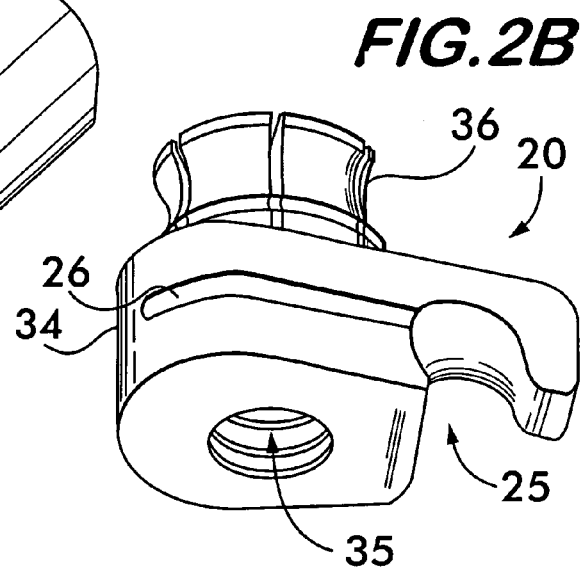

FIGS. 2A and 2B are upper and lower perspective views of a lower clamping member 20. It comprises a C-shaped spinal rod receiving channel 25 sized to accept a spinal rod 12. A slot 26 that runs the full depth of the clamping member 20 from the front side walls 28 to the rear sidewall 30 is in communication with the C-shaped channel. The slot 26 also runs from the C-shaped channel 25 almost to the rear wall 32 of the clamping body. However, it stops short of the rear wall 32 leaving a portion of material that essentially comprises a hinge 34 around which the slot 26 and the C-shaped channel 25 can be caused to open and close slightly.

In a preferred embodiment of the invention, the opening of the C-shaped channel 25 is slightly smaller than the diameter of the spinal rod 12 such that the spinal rod needs to be forced into the channel in a snapping-type action. Particularly, the hinge 34 will spread slightly under the force of pushing the rod into the channel 25, thus allowing the opening to the channel to spread slightly and permit the rod to be inserted into the channel. Once the largest cross-section of the rod passes the opening, the opening will snap shut again to its rest spacing. By making the opening slightly smaller than the diameter of the rod, when snapped in, the rod is loosely secured in the channel so that it cannot inadvertently fall out through the opening, but can be rotated and/or slid longitudinally in the channel 25. This permits full adjustability of the spacing between the clamping member pairs 16 and permits the transverse rod 14 to be rotated while minimizing the likelihood of the rod 14 inadvertently coming out of the clamping bodies 18.

The clamping member 20 further comprises a screw hole 35 that orthogonally intersects the slot 26. The screw hole 35 is threaded only in the portion that lies below the slot 26.

Extending outwardly from the clamping member 20 and coaxial with the screw hole 35 is a cylindrical collar 36 comprising a plurality of resilient flanges 36a separated from each other by slots 36b. Preferably, the collar 36 includes a circumferential groove 38. Also preferably, the upper ends of flanges define an angled or chamfered surface that can mate with a chamfered surface at the bottom of the head of a screw.

Figure 3:
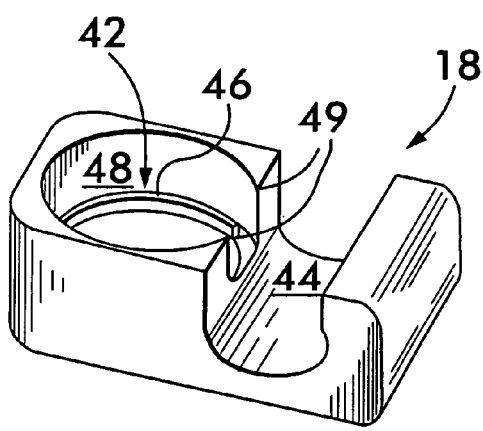
FIG. 3 is a perspective view of the upper clamping body of a clamping body pair of FIG. 1.

FIG. 3 is a perspective view of one of the upper clamps 18. It also comprises a C-shaped channel 44 accepting the transverse rod 14. In a preferred embodiment, the opening at the top of the C-shaped channel is slightly smaller than the diameter of the transverse rod. Hence, the rod would need to be snapped into the channel. The upper clamping member 18 also includes a screw hole 42 extending transversely to the C-shaped rod channel 44. Preferably, the screw hole 42 is not threaded. Furthermore, it is countersunk at its top end as shown at 48. The screw hole 42 is orthogonal to the C-shaped channel and is positioned so that a relatively small angular section 49 of that hole 42 intersects the C-shaped channel 44. This leaves a gap in an angular region of the upper portion the screw hole 42.

Figure 4:
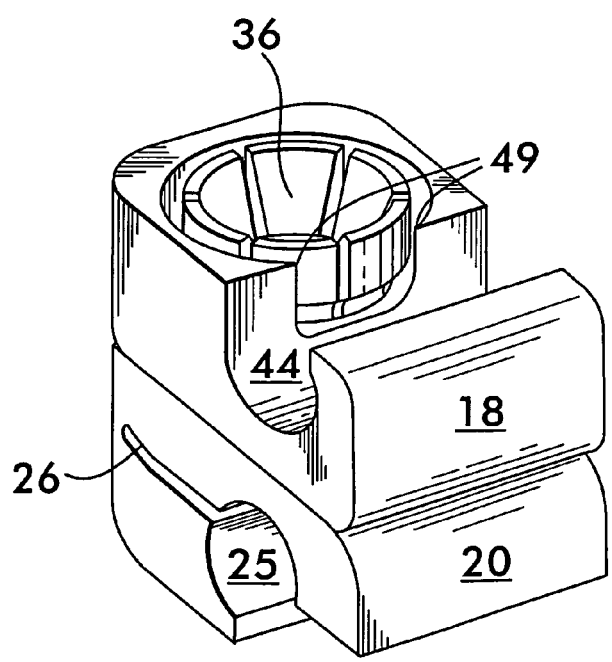
FIG. 4 is a perspective view of the lower and upper clamping bodies forming a clamping body pair in accordance with the present invention joined together prior to insertion of a screw.

Even further, a circumferential bead 46 is positioned in the screw hole. The bead 46 is positioned so as to mate with the groove 38 when the upper clamp 18 and a lower claim 20 are assembled together. Specifically, in order to assemble the two clamping bodies 18 and 20 together, the collar 36 of the lower clamping body 20 is longitudinally inserted into the hole 42 of the upper clamping body as shown in FIG. 4. The diameter of the hole 42 in the upper clamping body 18 is sized to accommodate the collar 36 generally without significant resistance. However, the smallest diameter defined by the bead 46 is slightly smaller than the outer diameter of the collar 36. Therefore, as the collar 36 is inserted into the hole 42, the flanges 36a are flexed slightly inwardly until the bead 46 meets the groove 38, at which point the flanges 36a can snap outward thus mating the bead 46 and the groove 38. This design loosely joins the upper clamp 18 and lower clamp 20 and prevents them from inadvertently becoming unassembled from each other, yet permits the two clamping members to be rotated relative to each other about the longitudinal axis of their coaxial screw holes.

FIG. 5 shows the screw 50 that can be inserted into the coaxial screw holes of the two clamping members 18, 20 in order to fix them to each other. The screw 50 comprises a head portion 52 having a chamfered lower surfaces 54 and a threaded shank portion 56. Preferably, the upper portion of the shank 58 that would sit inside the collar portion 36 of the lower clamping member 20 is not threaded.

FIG. 6 is another perspective view of the upper clamp 18 and the lower clamp 20 assembled together, but this time with the screw 50 threaded into the screw holes. When the screw 50 is inserted into the clamping members through the top of the collar 36, the threads of its threaded portion 56 will engage with the mating threads of screw hole 35 in the lower clamping member. As the screw 50 is rotated to advance it into the lower clamping member 20, the chamfered bottom 54 of the head 52 of the screw will hit the chamfered inner surface of the tops of the flanges 36a and spread the flanges outwardly. This will cause two things to happen. First, the outer surfaces of the flanges 36a will bear against the chamfered inner surface of the screw hole in the upper clamping member 18, thus locking the two clamping members 18, 20 together in their given relative angular orientation. Second, the one or more flanges 36a that are adjacent the cutout portion 49 of the screw hole 42 of the upper clamping member 18 will bear against the rod 14 that is sitting in the C-shaped channel locking it in place in the C-shaped channel. The flanges are particularly effective in locking the various components together because the sharp edges of the flanges dig into the inner wall of the screw hole 42 in the upper clamp 18 and into the transverse rod 14.

Simultaneously as the screw 50 is tightened, it squeezes closed the slot 26 and C-shaped channel 25 in the lower clamping member 20, thus clamping the spinal rod 12 securely in the lower clamping member 20. Thus, by the tightening of a single screw, both rods are caused to be locked in the clamping assembly and the angular orientations of the two rods also is fixed.

FIG. 7 is a plain view showing the rod to rod connector 10 of the present invention being used to interconnect to spinal rods that are not perfectly parallel to each other. It should be clear from the foregoing description that the rod to rod connector 10 of the present invention is very simple to operate, requiring the tightening of only two screws to completely assemble the apparatus as well as couple it to the spinal rods. Furthermore, it is a very simple structure comprising a total of seven components, namely, two lower clamps 20, two upper clamps 18, two screws 50 and the transverse rod 14. Also, it permits infinite angular positioning of the transverse rod 14 relative to either of the two spinal rods 12. Even further, it provides extremely tight clamping of all of the rods to the clamping bodies as well as the angular orientation of the upper and lower clamping bodies to each other.

Various modifications of the design are contemplated. For instance, in a first alternative embodiment shown in FIG. 8, the flanges 36a' of the collar 36' of the lower clamping member 20' may have a curvilinear outer surface so as to be shaped to have even greater surface contact with the transverse rod positioned in the C-shaped rod receiving channel 44 of the upper clamp.

Figure 9A:
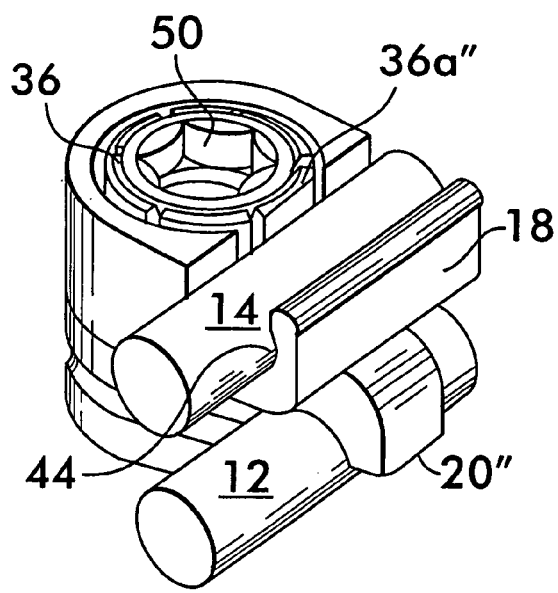
FIGS. 9A and 9B are perspective views of a rod to rod connector in accordance with another alternative embodiment of the present invention.
Figure 9B:
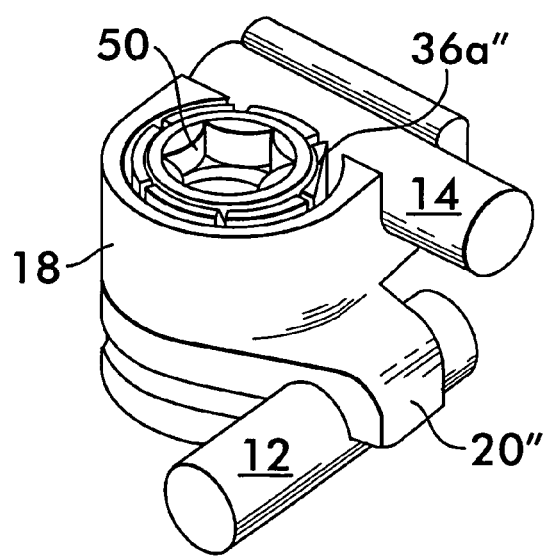

In another alternative embodiment shown in FIGS. 9A and 9B, an angular portion 91 of the outer surface of the collar 36", for instance, one of the flanges 36a", of the lower clamping member 90 may be flattened in order to permit the transverse rod 14 to be dropped into the C-shaped transverse rod channel 44 of the upper clamping member without resistance, i.e., without the need to flex one or more of the flanges in order to insert the rod. Preferably, this flattened portion is parallel to the C-shaped spinal rod receiving channel of the lower clamping member. Thus, the transverse rod 14 can be dropped into the C-shaped transverse rod channel 44 of the upper clamping member 18 when the upper clamping member is oriented relative to the lower clamping member so that the C-shaped channel of the upper clamping member is parallel to the C-shaped channel of the lower clamping member, as shown in FIG. 9A. Then, the upper clamping member can be rotated relative to the lower clamping member to a position where the two C-shaped channels are approximately orthogonal to each other (i.e., the general position in which almost all of the rods ride connectors will ultimately be deployed in situ) as shown in FIG. 9B. In this manner, the transverse rod can be easily placed in the upper clamping member 18 but will essentially immediately be rotated to a position in which it is captured in the clamping assembly 16 and cannot fall out, but is still longitudinally slidable and rotatable in the C-shaped channel of the upper clamping member. This feature is helpful for placing the assemblies on the transverse rod and then placing the rod to rod connector onto the spinal rods.

Figure 10:
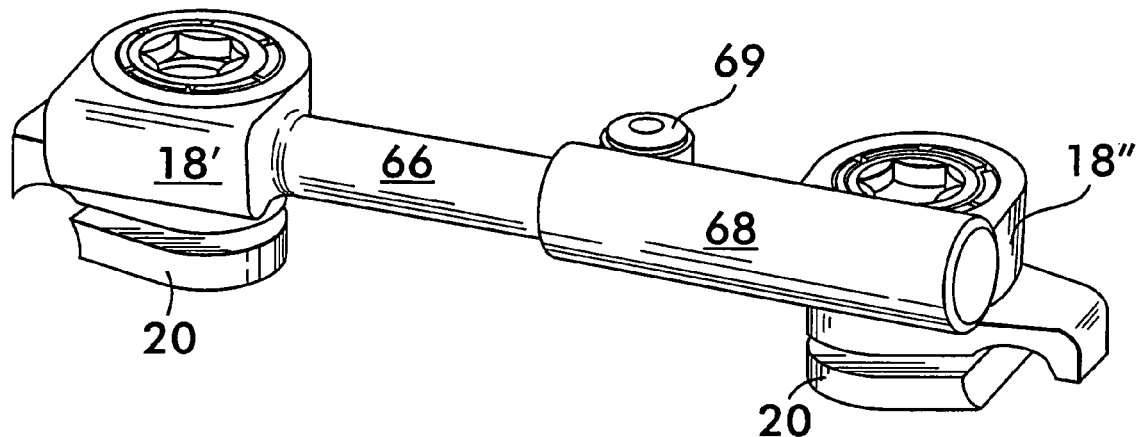
FIG. 10 is a perspective view of a rod to rod connector in accordance with another alternative embodiment of the present invention.

In yet another embodiment of the present invention shown in FIG. 10, the need for separate transverse rod 14 is eliminated by means of modified upper clamping members 18' and 18". As shown in FIG. 10, one of the upper clamps 18' includes an integral post 66. The other upper clamp 18" integrally comprises a tubular hollow shaft 68 for slidingly accepting the post 66 at various distances of insertion. A mechanism, such as a screw 69 and associated screw hole, are provided to lock the post 66 in the shaft 68 at a selected distance. The tubular shaft 68 may be split such that tightening the screw 69 in the screw hole squeezes the shaft 68 to a smaller diameter thus grasping the post 66. Alternatively, the screw may be positioned in a threaded hole in the shaft so that the distal end of the screw, when tightened, will bear directly on the post, thus locking the shaft and the post together at the selected distance. Other means for fixing the distance between the two pairs of clamping assemblies are well known in the prior art.

Figure 11:
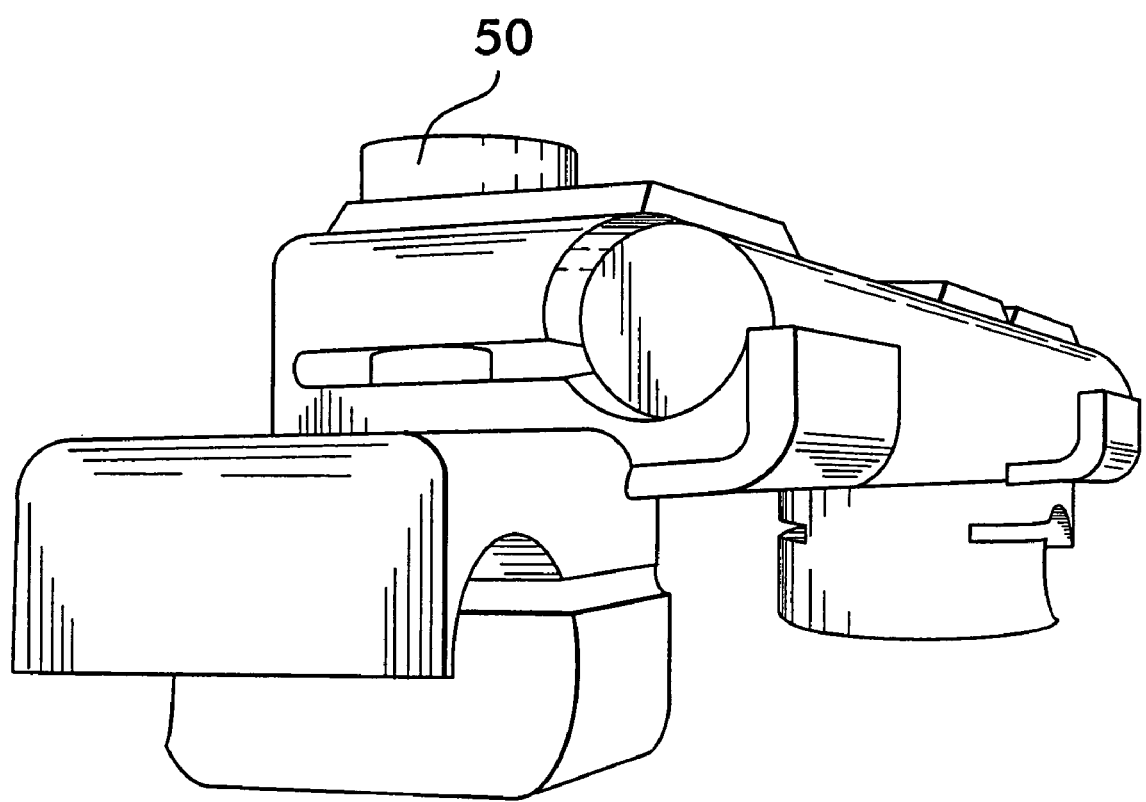
FIG. 11 is a perspective view of another rod to rod connector in accordance with yet another alternative embodiment of the present invention.

In another variation of the present invention, the upper and lower clamps are identical to each other and take the form of the lower clamp described above in connection with FIGS. 1-3, except that one or both of the clamps do not include the collar 36. A rod to rod connector in accordance with this embodiment is shown in FIG. 11. In this particular embodiment, neither clamping member includes a collar, although one of them could. In this embodiment, both clamping members lock their respective rods in place by action of the screw 50 closing the hinge so as to squeeze the slots and channels together.

Figure 12A:
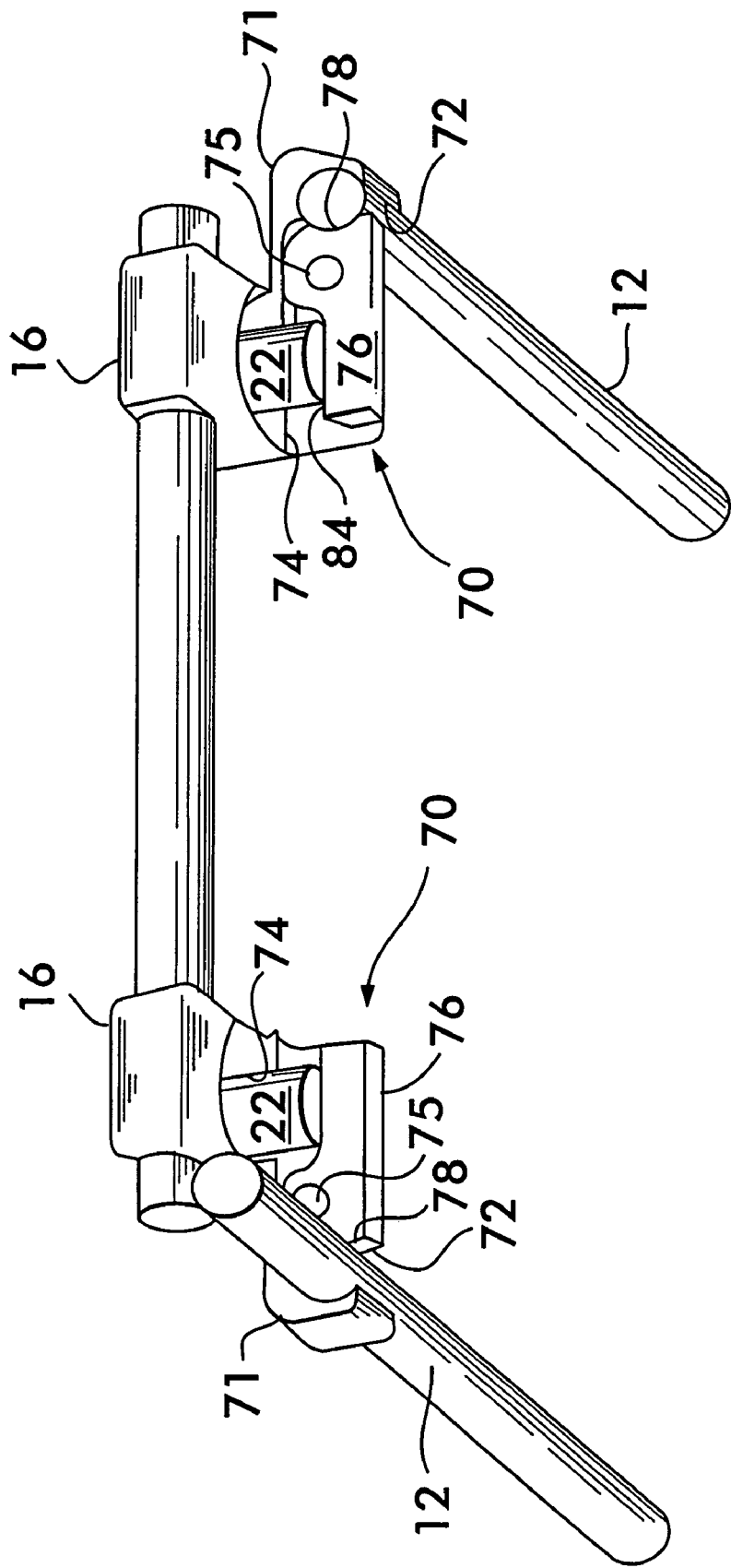
FIG. 12A is a perspective view of another rod to rod connector in accordance with yet another alternative embodiment of the present invention in which the lower clamping element is shown in cross section.

FIGS. 12A and 12B are two different perspective views of a rod to rod connector in accordance with yet one more embodiment of the present invention. In FIG. 12A, the lower clamping member is shown in partial cutaway.

The upper clamping element 16 can be the same as in the embodiment of FIG. 1. In this embodiment, the lower clamping member 70 comprises body 71, a channel 72 for accepting the spinal rod 12, a collar 73 essentially identical to the collar 36 previously described, a hole 74, a lever member 76 rotatably mounted to the body 72 via a pivot pin 75. Unlike the first embodiment disclosed hereinabove, in this embodiment, the hole 74 is threaded near the top of the hole and is not threaded near the bottom of the hole. The pivot pin 75, screw hole 72, and spinal rod channel 72 are all mutually orthogonal to each other.

The lever member 76 has a first end 78 that is a bearing surface that forms part of the channel 72 for the spinal rod 12. Preferably, the bearing surface is cylindrical and of a diameter equal to that of the spinal rod 12. The other end of the lever member 76 is another bearing surface 84 that is positioned in the way of the screw 22 so that, when the screw 22 is tightened, it bears down on the bearings surface 84 of the wedge member forcing the wedge member 76 to rotate about the pivot pin 75, thus causing the other end 80 to fixedly clamp the spinal rod 12.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A transverse connector for rigidly connecting first and second spinal rods to each other comprising:
   a transverse connecting member;
   a first clamping assembly for rigidly attaching said transverse connecting member to a first spinal rod, said first clamping assembly comprising:
   a first clamping body including a first channel for receiving said first spinal rod;
   a second clamping body including a second channel for receiving said transverse connecting member and a hole transverse to said second channel; and
   a collar extending from said first clamping body into said hole of said second clamping body, said collar comprising a plurality of resilient flanges; and
   a second clamping assembly for rigidly attaching said transverse connecting member to a second spinal rod,
   said first clamping body further comprising a hole coaxial with and through said collar, said hole being at least partially threaded and comprising a screw extending through said hole of said first clamping body and said hole of said second clamping body for connecting said first and second clamping bodies together,
   wherein said screw comprises a head and a threaded shank and wherein a portion of said hole of said second clamping body intersects said second channel of said second clamping body such that said head of said screw will bear against the transverse connecting member disposed in said second channel of said second clamping body thereby rigidly fixing said transverse connecting member in said second channel.

2. The transverse connector of claim 1 wherein said first channel for receiving said spinal rod further comprises a hinge whereby said first channel can be reduced in size around said spinal rod when said screw is tightened into said hole in said first clamping body.

3. The transverse connector of claim 2 wherein said first channel of said first clamping body comprises a C-shaped channel for accepting said spinal rod, and a slot intersecting said C-shaped channel at one end, said hinge being formed of material of said first clamping body at a second end of said slot.

4. The transverse connector of claim 3 wherein said hole of said first clamping body intersects said slot perpendicularly to said slot and comprises threads only below said slot.

5. A transverse connector for rigidly connecting first and second spinal rods to each other comprising:
   a transverse connecting member;
   a first clamping assembly for rigidly attaching said transverse connecting member to a first spinal rod, said first clamping assembly comprising:
   a first clamping body including a first channel for receiving said first spinal rod;
   a second clamping body including a second channel for receiving said transverse connecting member and a hole transverse to said second channel; and
   a collar extending from said first clamping body into said hole of said second clamping body, said collar comprising a plurality of resilient flanges; and
   a second clamping assembly for rigidly attaching said transverse connecting member to a second spinal rod,
   wherein the first channel is a hinged channel for receiving said first spinal rod, and the first clamping body comprises a screw hole transverse to said hinged channel, said screw hole being at least partially threaded, the hole of the second clamping body comprising a screw hole transverse to said second channel, said screw hole of the second clamping body being coaxially arranged with said screw hole of said first clamping body, the transverse connector further comprising a screw extending through said screw holes of said first and second clamping bodies for connecting said first and second clamping bodies together and squeezing said hinged channel to close around and clamp a rod disposed in said channel of said first clamping body.

6. The transverse connector of claim 5 wherein the collar extends from said first clamping body coaxially with said screw hole of said first clamping body, said collar comprising a plurality of resilient flanges adapted to fit within said screw hole of said second clamping body.

7. The transverse connector of claim 6 wherein said screw head bears against said transverse connecting member through said collar.

8. The transverse connector of claim 1 wherein said second clamping assembly comprises:
- a third clamping body including a third channel that is a hinged channel for receiving said second spinal rod, and a screw hole transverse to said third channel, said screw hole being at least partially threaded;
- a fourth clamping body including a fourth channel for receiving said transverse connecting member and a screw hole transverse to said fourth channel, said screw hole being coaxially arranged with said screw hole of said first clamping body; and
- a second screw extending through said screw holes of said third and fourth clamping bodies for connecting said third and fourth clamping bodies together and squeezing said hinged channel to close around and clamp a rod disposed in said channel of said third clamping body.

9. A transverse connector for rigidly connecting first and second spinal rods to each other comprising:
- a transverse connecting member;
- a first clamping assembly for rigidly attaching said transverse connecting member to a first spinal rod, said first clamping assembly comprising:
- a first clamping body including a first channel for receiving said first spinal rod;
- a second clamping body including a second channel for receiving said transverse connecting member and a hole transverse to said second channel; and
- a collar extending from said first clamping body into said hole of said second clamping body, said collar comprising a plurality of resilient flanges; and
- a second clamping assembly for rigidly attaching said transverse connecting member to a second spinal rod,
- the transverse connector further comprising a screw, the hole of the second clamping body accepting said screw, the first clamping body further comprising a hole, a pivot pin, a lever member coupled to said first clamping body by said pivot pin, said lever member comprising first and second longitudinal ends, said first end positioned to be rotated about said pivot pin by advancement of said screw into said hole of said second clamping body, said second end positioned to bear against said rod and clamp said rod in said first channel upon said lever member being rotated by said screw, wherein said holes in said first and second clamping bodies are coaxial so that said screw can be advanced through said holes to join together said first and second clamping bodies.

* * * * *

UNITED STATES PATENT AND TRADEMARK OFFICE
CERTIFICATE OF CORRECTION

PATENT NO. : 7,628,799 B2  Page 1 of 1
APPLICATION NO. : 11/221512
DATED : December 8, 2009
INVENTOR(S) : Richelsoph et al.

It is certified that error appears in the above-identified patent and that said Letters Patent is hereby corrected as shown below:

At Column 9, line 1, please replace "The transverse connector of claim 1" with "The transverse connector of claim 5".

Signed and Sealed this

Sixteenth Day of March, 2010

David J. Kappos
*Director of the United States Patent and Trademark Office*